(12) United States Patent
Kim

(10) Patent No.: US 12,201,756 B2
(45) Date of Patent: Jan. 21, 2025

(54) LOW TEMPERATURE MICRO PLASMA OZONE GENERATING DEVICE

(71) Applicant: CAST CO., LTD., Seoul (KR)

(72) Inventor: Min Hwan Kim, Seoul (KR)

(73) Assignee: CAST CO., LTD., Seoul (KR)

( * ) Notice: Subject to any disclaimer, the term of this patent is extended or adjusted under 35 U.S.C. 154(b) by 626 days.

(21) Appl. No.: 17/619,520

(22) PCT Filed: Jun. 15, 2021

(86) PCT No.: PCT/KR2021/007446
§ 371 (c)(1),
(2) Date: Dec. 15, 2021

(87) PCT Pub. No.: WO2022/045546
PCT Pub. Date: Mar. 3, 2022

(65) Prior Publication Data
US 2022/0370677 A1    Nov. 24, 2022

(30) Foreign Application Priority Data

Aug. 27, 2020   (KR) .................. 10-2020-0108443

(51) Int. Cl.
*A61L 9/22*      (2006.01)
*C01B 13/11*     (2006.01)
*H05H 1/24*      (2006.01)

(52) U.S. Cl.
CPC ............... *A61L 9/22* (2013.01); *C01B 13/11* (2013.01); *H05H 1/2406* (2013.01)

(58) Field of Classification Search
CPC ...... A61L 9/22; A61L 9/015; A61L 2209/212; C01B 13/10; C01B 13/11; H05H 1/2406; H05H 1/2437; H05H 2245/15
See application file for complete search history.

(56) References Cited

U.S. PATENT DOCUMENTS

2015/0270110 A1* 9/2015 Eden .................. A23L 3/34095
422/186.04

\* cited by examiner

*Primary Examiner* — Lessanework Seifu
(74) *Attorney, Agent, or Firm* — NKL Law; Byungwoong Park

(57) ABSTRACT

A low temperature micro plasma ozone generating device for generating ozone by inhaling external air and reacting the sucked air with plasma. The low temperature micro plasma ozone generating device includes a main body having an accommodating space therein; an ozone generating module installed in an internal accommodation space of the main body to generate ozone; an external air supply line installed to be connected to the ozone generating module from an outside of the main body and configured to supply external air of the main body to an inside of the ozone generating module; an ozone discharge line installed to extend from the inside of the ozone generating module to the outside of the main body to discharge the ozone generated by the ozone generating module to the outside of the main body; and a cooling fan installed on one side of the main body.

3 Claims, 10 Drawing Sheets

[FIG.1]
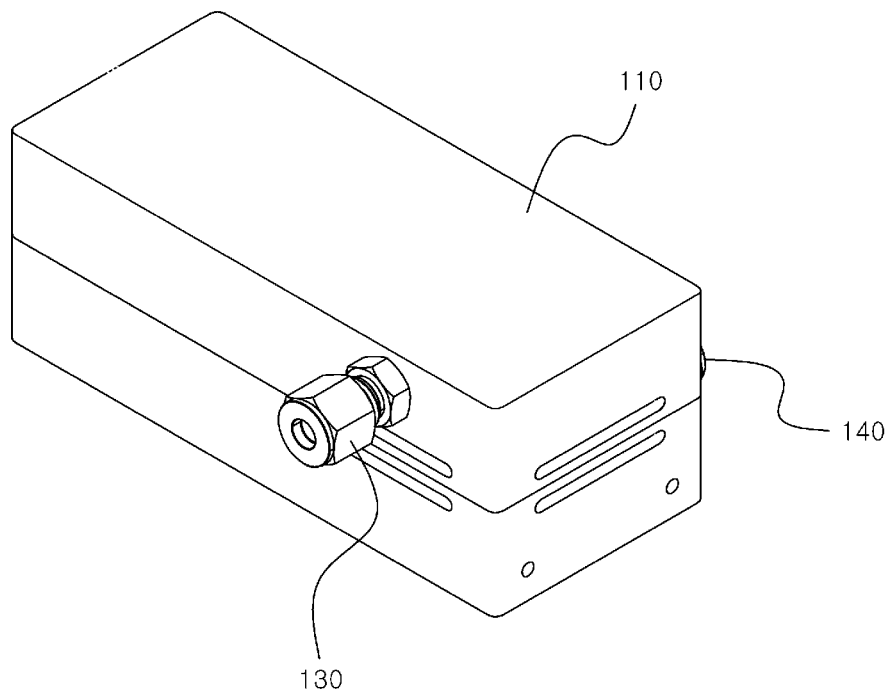
[FIG.2]
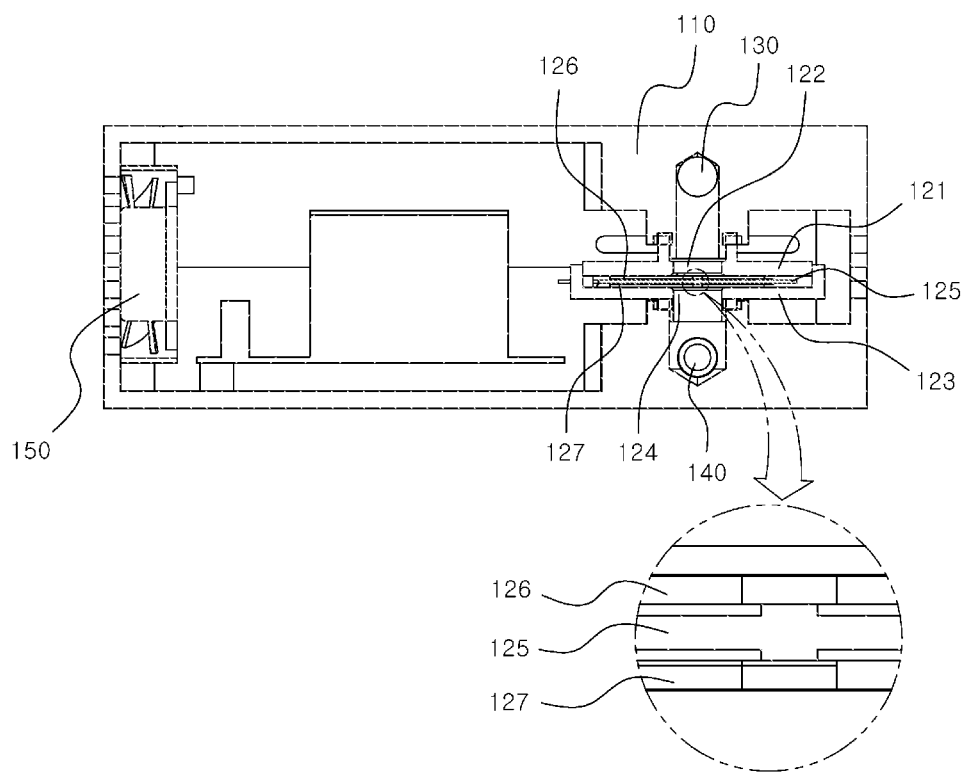

[FIG.3]
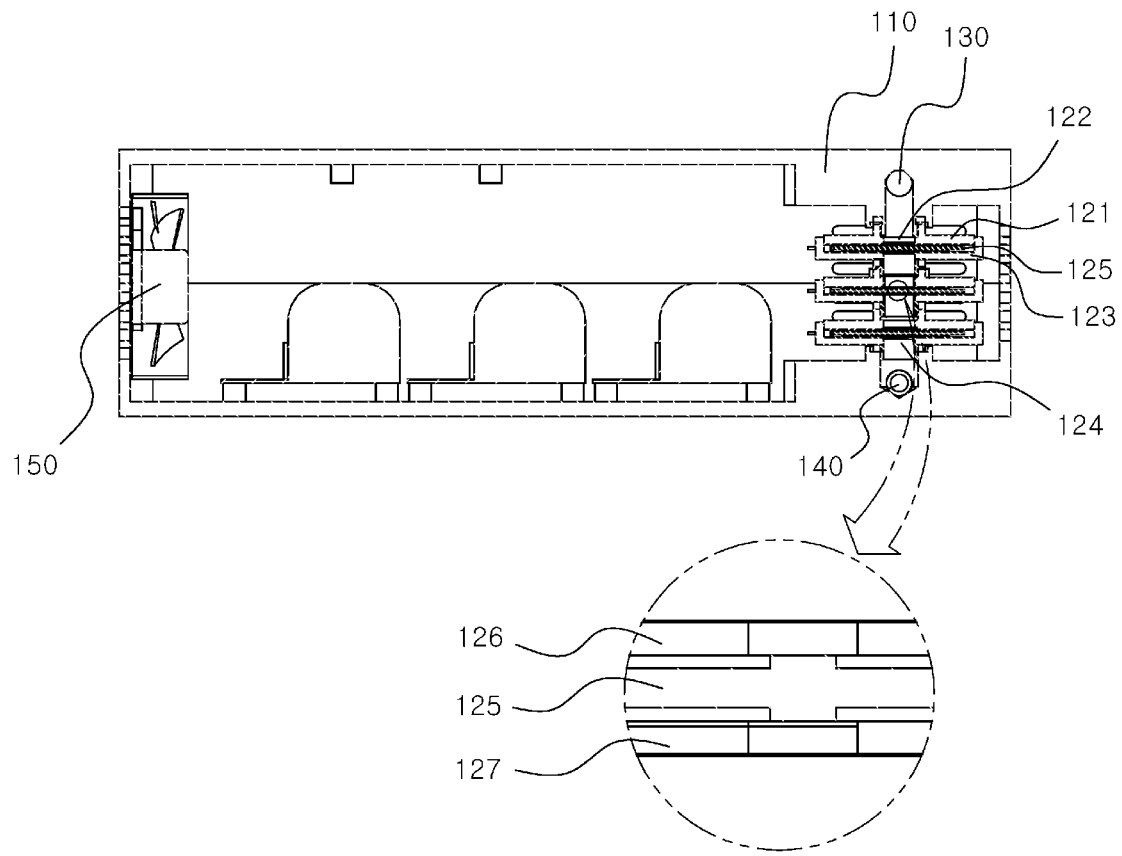
[FIG.4]
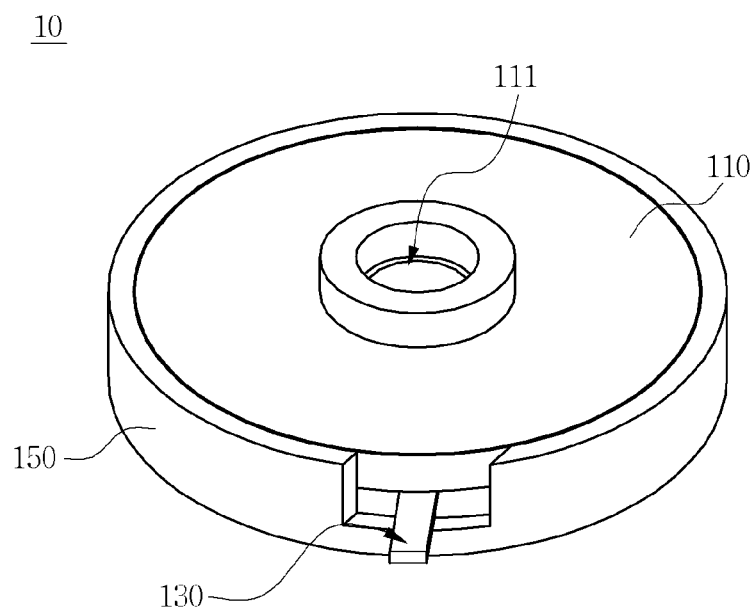

[FIG.5]
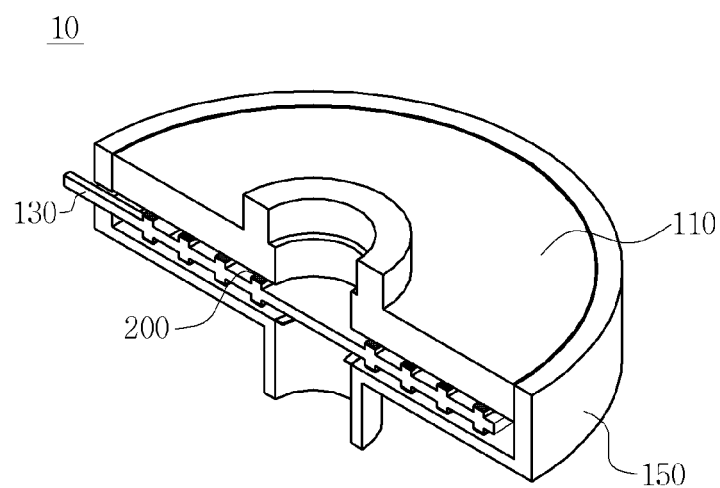

[FIG.6]
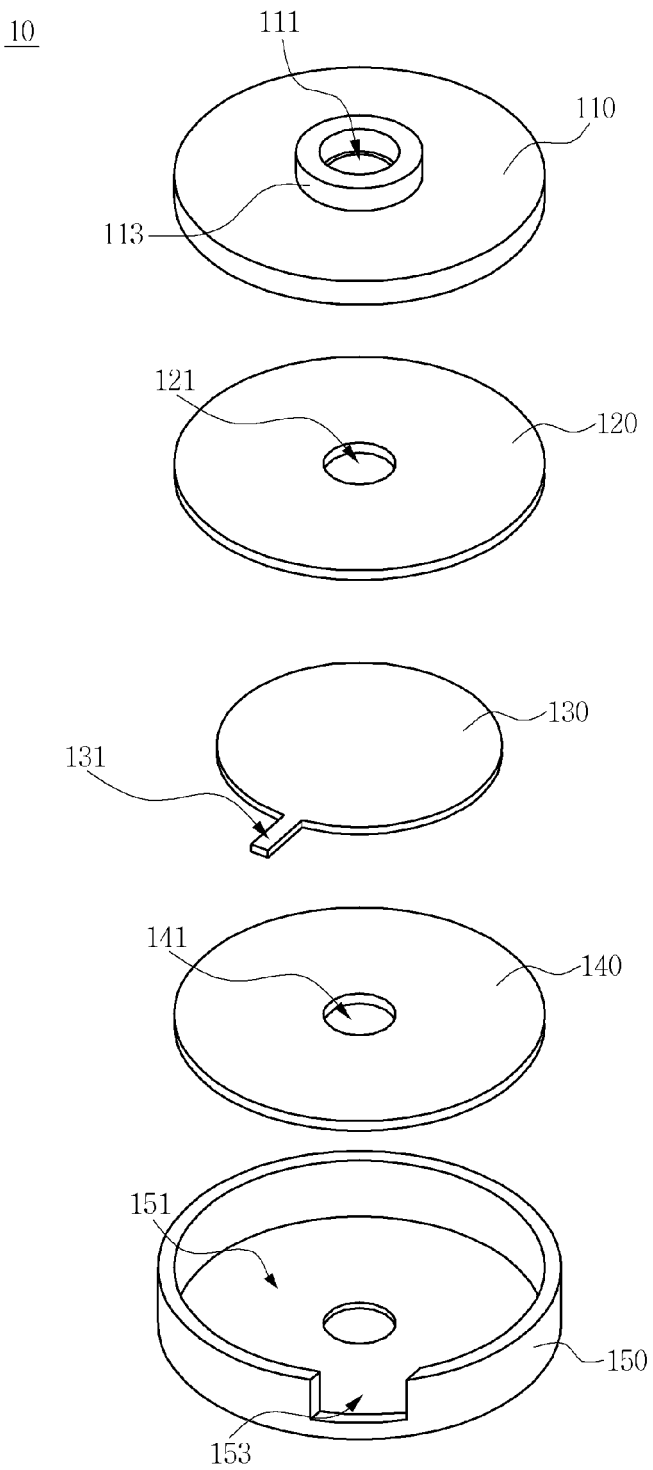

[FIG.7]
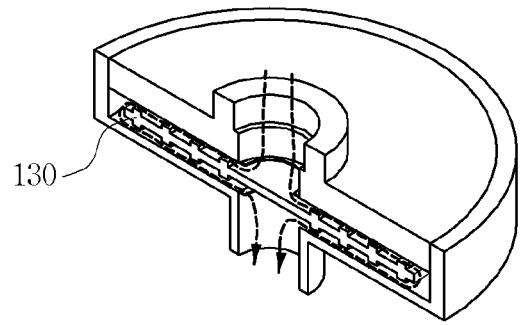
(a)
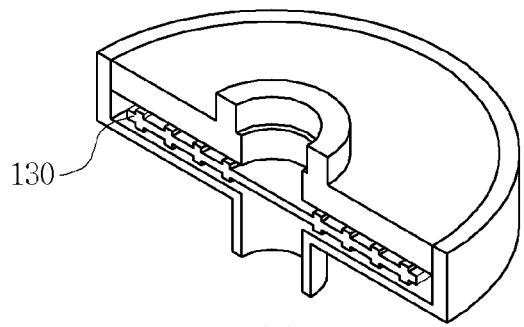
(b)
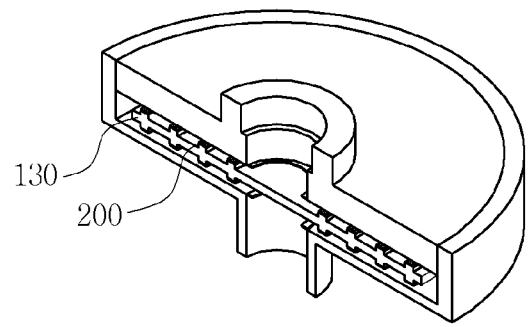
(c)

[FIG.8]
130a
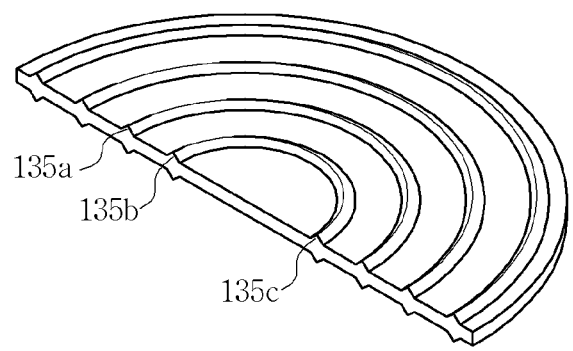
(a)
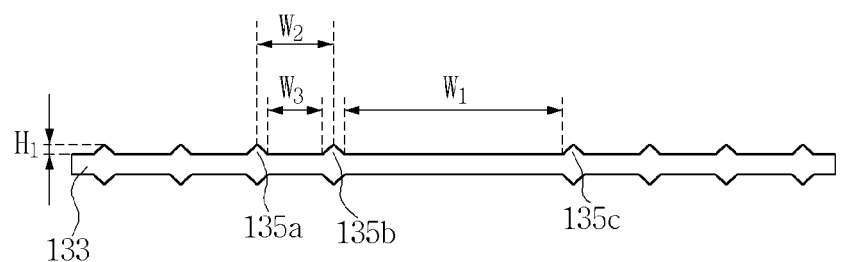
(b)

[FIG.9]
130b
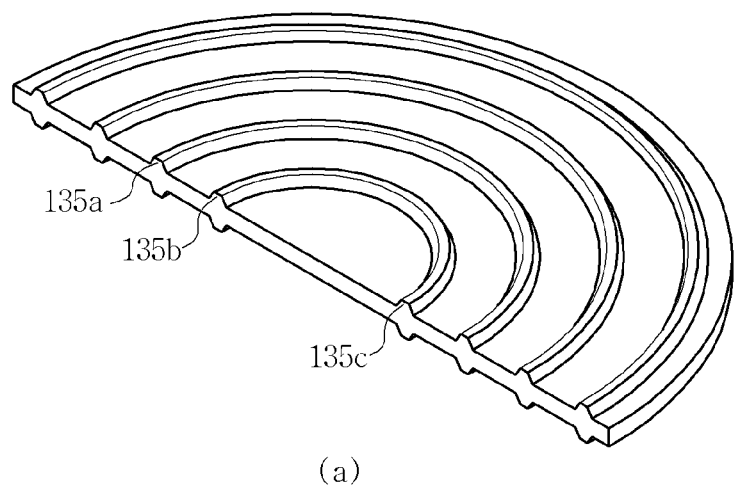
(a)
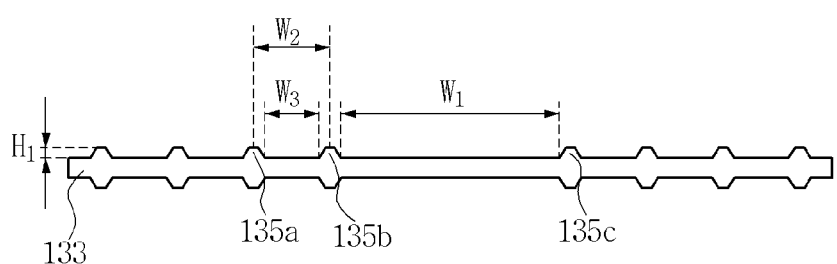
(b)

[FIG.10]
130c
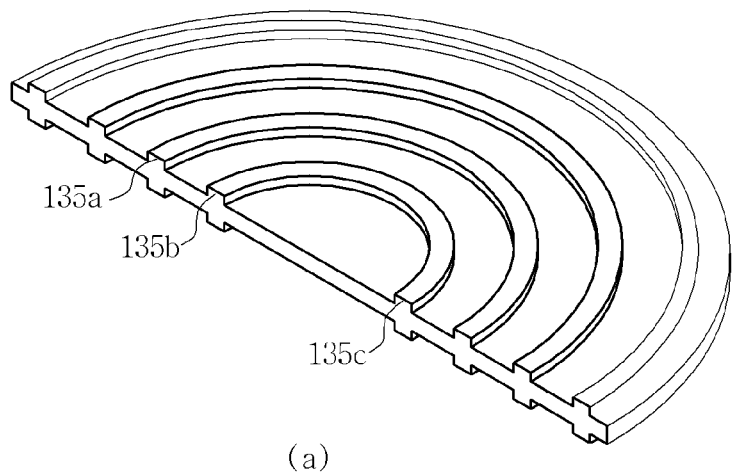
(a)
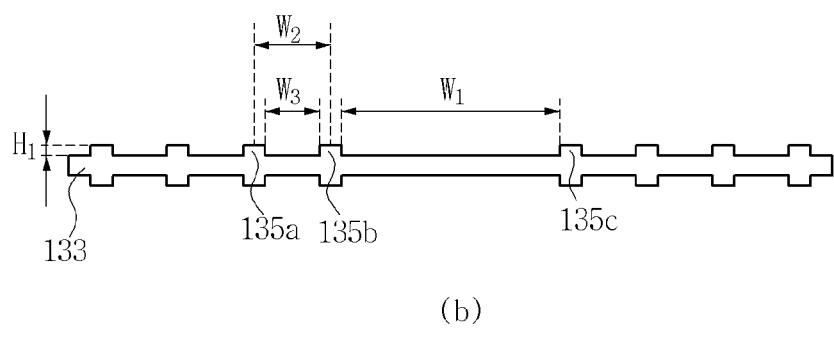
(b)

[FIG.11]
130d
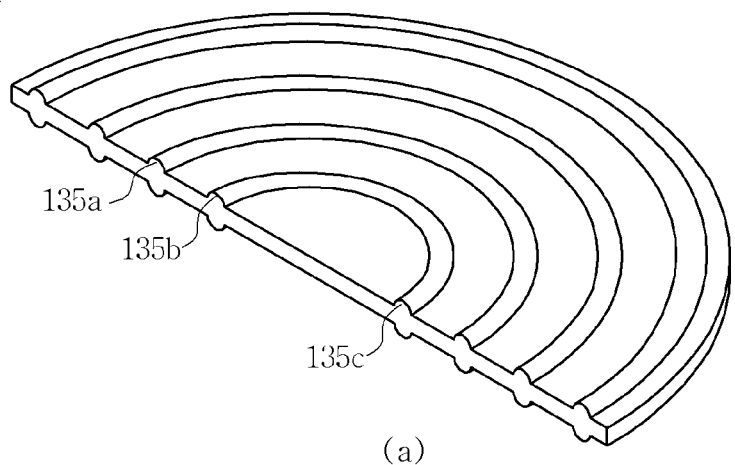
(a)
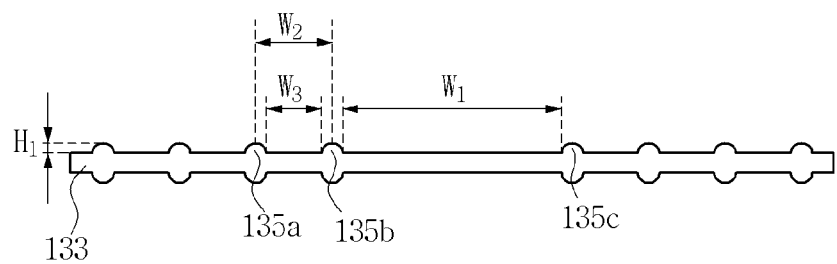
(b)

[FIG.12]
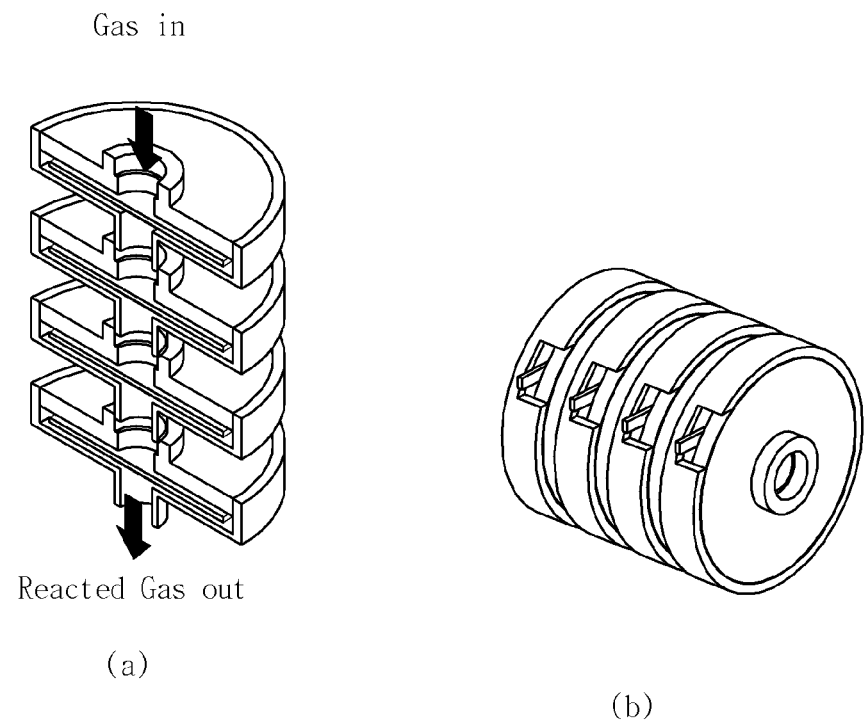

LOW TEMPERATURE MICRO PLASMA OZONE GENERATING DEVICE

FIELD

The present disclosure relates to a low temperature micro plasma ozone generating device and, more particularly, a low temperature micro plasma ozone generating device in which plasma is generated on a plurality of micro-patterns disposed between a plurality of floating electrodes and generating ozone by causing the plasma to react with air sucked from the outside.

BACKGROUND

Plasma is defined as the fourth state of matter solid, liquid, and gas according to the size of particles constituting the matter. When energy is applied to a solid, it becomes a liquid, and then, a gas. When high energy is applied to the gas substance, the gas is separated into electrons and atomic nuclei at tens of thousands of degrees Celsius, thereby becoming a plasma state.

In a plasma generated at a very high temperature, molecules are completely dissociated to become an atomic state, and all the electrons bound to atoms are released from their electron orbits as free electrons to become a gaseous state composed of ions and electrons. Yet, if the temperature of the plasma is not high, highly reactive chemical species (radicals) are generated due to completely dissociated molecules, incompletely ionized ionic molecules or ionic atoms, etc. In particular, there are various constituent elements such as low temperature ions, electrons, radicals, UV, etc., so its characteristics are very diverse.

The three control functions of activation, sterilization and catalysis induced by these various constituent elements may be used in various fields. For example, in agriculture, it is possible to improve the germination rate of seeds or the growth rate of sprouts, and it is possible to sterilize using active species and ultraviolet rays generated, so it can be used for food storage and distribution. Catalysis may promote the dissociation of molecules by electrons and active species, and may be applied to the decomposition of ethylene gas generated while fruits are stored.

A low temperature plasma has various constituent elements such as ions, electrons, active species, and ultraviolet rays due to its low temperature and thus has a variety of properties. This allows the three functions of activation, sterilization, and catalysis to be induced and used in a variety of applications.

An effective ozone generating device using micro plasmas may be used not only in large-capacity facilities, but also in low-capacity small facilities that have been difficult to access in the past. In addition, freshness of agricultural food is improved through the improvement of the agricultural food storage environment and the control of microorganisms according to various demands and needs, and sustainable agri-food technology is being developed in a customized way.

As a related art, there is Korean Patent No. 10-1839823 titled "MODULAR MICRO PLASMA MICROCHANNEL REACTOR DEVICES, MINIATURE REACTOR MODULES AND OZONE GENERATION DEVICES." However, Korean Patent No. 10-1839823 only discloses a technique of fabricating a microchannel in a non-insulator and generating a plasma in the channel by passing a gas through the channel.

SUMMARY

In view of the above, the present disclosure provides a low temperature micro plasma ozone generating device for generating ozone by generating plasma on a plurality of micro-patterns disposed between a plurality of floating electrodes, so that the generated ozone may remove pests, reduce ethylene, and sterilize harmful bacteria.

In an aspect, there is provided a low temperature micro plasma ozone generating including: a main body having an accommodating space therein; an ozone generating module installed in an internal accommodation space of the main body to generate ozone; an external air supply line installed to be connected to the ozone generating module from an outside of the main body and configured to supply external air of the main body to an inside of the ozone generating module; an ozone discharge line installed to extend from the inside of the ozone generating module to the outside of the main body to discharge the ozone generated by the ozone generating module to the outside of the main body; and a cooling fan installed on one side of the main body to supply the external air of the main body to an outer surface of the ozone generating module.

Accordingly, in the present disclosure, it is possible to generate a micro plasma with high discharge efficiency at a desired location through a double-sided high-voltage conductor having the micro patterns. In addition, it is possible to increase the amount of activated ions and active species by stacking a plurality of low temperature micro plasma ozone generating devices. In addition, ozone generated through low temperature micro plasma may be used to remove pests, reduce ethylene, and sterilize harmful bacteria. In addition, due to its small size, the low temperature micro plasma ozone generating device according to the present disclosure may be used by being attached to various types of storage devices, water treatment devices, and the like.

BRIEF DESCRIPTION OF THE DRAWINGS

FIG. 1 is a perspective view illustrating a low temperature micro plasma ozone generating device according to an embodiment of the present disclosure.

FIG. 2 is a cross-sectional view illustrating a low temperature micro plasma ozone generating device according to an embodiment of the present disclosure.

FIG. 3 is a cross-sectional view illustrating a low temperature micro plasma ozone generating device according to another embodiment of the present disclosure.

FIG. 4 is a perspective view illustrating a low temperature micro plasma generating device according to an embodiment of the present disclosure.

FIG. 5 is a cross-sectional view of a low temperature micro plasma generating device according to an embodiment of the present disclosure.

FIG. 6 is an exploded perspective view of a low temperature micro plasma generating device according to an embodiment of the present disclosure.

FIG. 7 is a view illustrating an operation of a low temperature micro plasma generating device according to an embodiment of the present disclosure.

FIG. 8 is a diagram illustrating micro-patterns of a high-voltage conductor according to an embodiment of the present disclosure.

FIG. 9 is a diagram illustrating micro-patterns of a high-voltage conductor according to an embodiment of the present disclosure.

FIG. 10 is a diagram illustrating micro-patterns of a high-voltage conductor according to an embodiment of the present disclosure.

FIG. 11 is a diagram illustrating micro-patterns of a high-voltage conductor according to an embodiment of the present disclosure.

FIG. 12 is a diagram in which low temperature micro plasma generating devices are stacked according to an embodiment of the present disclosure.

DETAILED DESCRIPTION

In embodiments according to the concept of the present disclosure disclosed in the specification, specific structural and functional descriptions are directed only to providing examples for describing the embodiments of the present disclosure, and the embodiments according to the concept of the present disclosure may be implemented in various forms, and the present disclosure is not limited to the embodiments described in the specification.

While the embodiments according to the concept of the present disclosure may be modified in various ways and have various alternative forms, examples of the embodiments are shown in the drawings and described in detail below. However, there is no intent to limit the present disclosure to the particular forms disclosed, and the present disclosure covers all modifications, equivalents, and alternatives falling within the spirit and scope of the present disclosure.

It will be understood that, although the terms "first," "second," etc. may be used herein to describe various elements, these elements should not be limited by these terms. These terms are only used to distinguish one element from another. For example, a first element could be called a second element, and a second element could similarly be called a first element without departing from the scope of the present disclosure.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements. Other words used to describe relationships between elements should be interpreted in a like fashion (i.e., "between" versus "directly between," "adjacent" versus "directly adjacent," and the like).

The terminology used herein to describe embodiments of the present disclosure is not intended to limit the scope of the present disclosure. The use of the singular form in the present document should not preclude the presence of more than one referent. In other words, elements of the present disclosure referred to in the singular may number one or more, unless the context clearly indicates otherwise. It will be further understood that the terms "comprise," "comprising," "include," and/or "including," when used herein, specify the presence of stated features, numbers, steps, operations, elements, components, and/or combinations thereof, but do not preclude the presence or addition of one or more other features, numbers, steps, operations, elements, components, and/or combinations thereof.

Unless defined otherwise, all terms used herein, including technical or scientific terms, have the same meaning as commonly understood by one of ordinary skill in the art to which this invention belongs. It should be further understood that terms in common usage should also be interpreted as is customary in the relevant art and not in an idealized or overly formal sense unless expressly so defined herein.

Hereinafter, exemplary embodiments of a low temperature micro plasma ozone generating device according to a preferred embodiment of the present disclosure will be described in detail with reference to the accompanying drawings.

FIG. 1 is a perspective view illustrating a low temperature micro plasma ozone generating device according to an embodiment of the present disclosure, and FIG. 2 is a cross-sectional view showing a low temperature micro plasma ozone generating device according to an embodiment of the present disclosure.

Referring to FIGS. 1 and 2, a low temperature micro plasma ozone generating device 100 includes a main body 110, an ozone generating module 120 installed in an inner accommodation space of the main body 110 to generate ozone, an external air supply line 130 installed to be connected to the ozone generating module 120 from the outside of the main body 110 and supplying external air of the main body 110 to the inside of the ozone generating module 120, an ozone discharge line 140 installed to extend from the inside of the ozone generating module 120 to the outside of the main body 110 and discharging ozone generated by the ozone generating module 120 to the outside of the main body 110, and a cooling fan 150 installed on one side of the main body 110 to supply air outside the main body 110 to an outer surface of the ozone generating module 120.

The main body 110 is a structure formed in a rectangular box shape, and has an accommodation space formed therein. In this case, a plurality of cooling slits are provided on one side of the main body 110 so that external air of the main body 110 may be introduced into the internal accommodation space of the main body 110.

The ozone generating module 120 includes: a circular first floating electrode 121 having an air inlet 122 installed to be connected to the external air supply line 130; a second floating electrode 123 coupled to the first floating electrode 121 and having an ozone outlet 124 installed to be connected to the ozone discharge line 140; a high-voltage conductor 125 disposed between the first floating electrode 121 and the second floating electrode 123 to generate plasma on a plurality of micro patterns; a first dielectric 126 disposed between the first floating electrode 121 and the high-voltage conductor 125; and a second dielectric 127 disposed between the high-voltage conductor 125 and the second floating electrode 123.

The first floating electrode 121 is a circular plate having a predetermined thickness, and the air inlet 122 is formed in the central portion to pass through the first floating electrode 121.

The second floating electrode 123 is also provided as a circular plate having a predetermined thickness, but is formed to have a larger diameter than that of the first floating electrode 121. A coupling groove for coupling with the first floating electrode 121 is formed in the second floating electrode 123 along an outer periphery. Accordingly, as the first floating electrode 121 is inserted into the coupling groove, the second floating electrode 123 is coupled to the first floating electrode 121. In this case, the ozone outlet 124 is formed in the central portion of the second floating electrode 123 to pass through the second floating electrode 123.

The high-voltage conductor 125 is a conductor capable of allowing a high voltage disposed between the first floating electrode 121 and the second floating electrode 123 to pass therethrough. A plurality of micro patterns are formed over the entire area of the high-voltage conductor 125, and plasma may be generated on the micro-patterns. In this case, the thickness of the generated micro plasma may be 50 μm to 300 μm, but not limited thereto. The shape of the micro-patterns may be at least one of a triangle, an equilateral quadrangle, a quadrangle, and a semicircle, but not limited thereto. According to an embodiment, a flat high-voltage conductor 125 having no micro-pattern may be disposed. The high-voltage conductor 125 secures a discharge space by adjusting the gap in between both sides of the high-voltage conductor 125 to a micro scale, and an electric field is strengthened near the gap to generate plasma. In particular, the present disclosure is designed to adjust a location where to generate plasma so that the plasma can be generated on a plurality of micro-patterns, and there is an effect that gas discharge efficiency improves by surface design configuration of various patterns. The high-voltage conductor 125 has a double-sided electrode structure, and may enhance the amount of discharge more than twice that of a single-sided electrode structure. In addition, the high-voltage conductor 125 is disposed within the first floating electrode 121 and the second floating electrode 123, so that stability may improve.

The first dielectric 126 and the second dielectric 127 are each a circular plate formed of a general dielectric material. The first dielectric 126 and the second dielectric 127 are installed to be disposed between the first floating electrode 121 and the high-voltage conductor 125 and between the high-voltage conductor 125 and the second floating electrodes 123, respectively.

In the ozone generating module 120 configured as described above, when air is introduced through the air inlet 122 of the first floating electrode 121, the air may flow from the center of the upper surface of the high-voltage conductor 125 to a side of the upper surface of the high-voltage conductor 125 and the air that has flown may flow from a side of the lower surface of the high-voltage conductor 125 to the center of the lower surface of the high-voltage conductor 130 and be then discharged through the ozone outlet 124 of the second floating electrode 123. In this case, plasma is generated in the micro-patterns of the high-voltage conductor 125, and ozone is generated by reaction of the plasma with the introduced air. The ozone generated as described above is discharged together with the air through the ozone outlet 124 of the second floating electrode 123.

FIG. 3 is a cross-sectional view illustrating a low temperature micro plasma ozone generating device according another embodiment of the present disclosure.

Referring to FIG. 3, an ozone generating module different from the ozone generating module shown in the embodiments of FIGS. 1 and 2 is illustrated. Referring to another embodiment of FIG. 3, a plurality of ozone generating modules 120 may be provided and installed in a stack. In this case, an ozone outlet 124 of one ozone generating module 120 is installed to be connected to an air inlet 122 of another ozone generating module 120 disposed thereunder. In addition, an air inlet 122 of an uppermost ozone generating module 120 is connected to the external air supply line 130, and an ozone outlet 124 of a lowermost ozone generating module 120 is connected to the ozone discharge line 140. As described above, when a plurality of ozone generating modules 120 are provided and formed in a stack, it is possible to generate a larger amount of ozone than when a single ozone generating module 120 is used.

The external air supply line 130 is a pipe having a predetermined diameter in which a transfer space is formed therein. One side of the external air supply line 130 is formed to protrude outward from the main body 110, and the other side of the external air supply line 130 is formed to be connected to an air inlet 122 of an ozone generating module 120 so as to introduce external air of the main body 110 into the inside of the ozone generating module 120.

In addition, the ozone discharge line 140 is a pipe having a predetermined diameter in which a transfer space is formed therein. One side of the ozone discharge line 140 is formed to be connected to an ozone outlet 124 of an ozone generating module 120, and the other side of the ozone discharge line 140 is formed to protrude outwardly from the main body 110 so as to discharge ozone generated by the ozone generating module 120 to the outside of the main body 110.

The cooling fan 150 is disposed near the plurality of cooling slits of the main body 110 and operated to supply external air of the main body 110 to an ozone generating module 120 through the cooling slits. As described above, the external air of the main body 110 is supplied to an ozone generating module 120 by the cooling fan 150 to cool the ozone generating module 120 heated up by generation of ozone.

As described above, preferred embodiments of the micro plasma ozone generating device according to the present disclosure have been described.

FIG. 4 is a perspective view illustrating a low temperature micro plasma generating device according to an embodiment of the present disclosure.

Referring to FIG. 4, a low temperature micro plasma generating device 10 includes a first floating electrode 110, a high-voltage conductor 130, and a second floating electrode 150. The first floating electrode 110 may have a gas inlet 111 in an upper central portion thereof so that gas can be introduced.

The second floating electrode 150 may be coupled to the first floating electrode 110, and a gas outlet (not shown) may be provided in a lower central portion of the second floating electrode 150. Accordingly, the introduced gas may react with plasma, discharging a reactant. The second floating electrode 150 may have an opening on one side thereof, and a protrusion of the high-voltage conductor may pass through the opening to be exposed outward.

The high-voltage conductor 130 is disposed between the first floating electrode 110 and the second floating electrode 150 and may generate plasma on a plurality of micro patterns. In this case, the thickness of the generated micro plasma may be 50 μm to 300 μm, but not limited thereto. The shape of the micro-patterns may be at least one of a triangle, an equilateral quadrangle, a quadrangle, and a semicircle, but not limited thereto. According to an embodiment, a flat high-voltage conductor 130 having no micro pattern may be disposed.

FIG. 5 is a cross-sectional view of a low temperature micro plasma generating device according to an embodiment of the present disclosure. Referring to FIG. 5, a cross-sectional view of the central portion of a low temperature micro plasma generating device 10 is provided, in which a high-voltage conductor 130 is disposed between a first floating electrode 110 and a second floating electrode 150. The high-voltage conductor 130 includes a plurality of micro patterns. The high-voltage conductor 130 secures a discharge space by adjusting the gap in between both sides of the high-voltage conductor to a micro scale, and an electric field is strengthened near the gap to generate plasma. In particular, the present disclosure is designed to adjust a location where to generate plasma so that the plasma can be generated on a plurality of micro-patterns, and there is an effect that gas discharge efficiency improves by surface design configuration of various patterns.

The high-voltage conductor 130 has a double-sided electrode structure, and may enhance the amount of discharge more than twice that of a single-sided electrode structure. In addition, the high-voltage conductor 130 is disposed within the first floating electrode 110 and the second floating electrode 150, so that stability may improve.

FIG. 6 is an exploded perspective view of a low temperature micro plasma generating device according to an embodiment of the present disclosure. Referring to FIG. 6, a low temperature micro plasma generating device 10 includes: a first floating electrode 110 having a gas inlet port 113 to form a gas inlet 111; first dielectric 126 disposed between the first floating electrode 110 and a high voltage conductor 130 and having an open area 121; the high voltage conductor 130 having a protrusion 131; a second dielectric 140 disposed between the high voltage conductor 130 and a second floating electrode 150 and having an open area 141; the second floating electrode 150 having an opening on one side thereof so that the protrusion of the high voltage conductor is exposed outwardly, and having an open space 151 where the high voltage conductor 130 is disposed.

FIG. 7 is a view illustrating an operation of a low temperature micro plasma generating device according to an embodiment of the present disclosure.

Referring to FIG. 7(a), in a low temperature micro plasma generating device, when gas is first introduced through a gas inlet 111 of a first floating electrode 110, the gas may flow from the center of the upper surface of a high-voltage conductor 130 to a side of the upper surface of the high-voltage conductor 130 and the gas that has flown may flow from a side of the lower surface of the high-voltage conductor 130 to the center of the lower surface and be then discharged through the gas outlet of a second floating electrode 150.

FIG. 7(b) is a view illustrating the low temperature micro plasma generating device 10 before generation of plasma, and FIG. 7(c) is a view illustrating the low temperature micro plasma generating device 10 after generation of plasma. In FIG. 7(c), micro plasma 200 may be generated on micropatterns, and introduced gas may react with the micro plasma 200 to thereby discharge a reactant.

FIGS. 8 to 11 are diagrams illustrating micro-patterns of a high-voltage conductor according to an embodiment of the present disclosure.

Referring to FIGS. 8 to 11, a high-voltage conductor 130 may include a plurality of micro patterns. The plurality of micro-patterns may form circular patterns having different diameters from the center point. In this case, a horizontal width in the plurality of micro patterns may be in the range of 40 to 60 µm. A height of the plasma generated on the plurality of micro-patterns may be in the range of 50 to 300 µm.

Referring to FIGS. 8(a) and 8(b), a high-voltage conductor 130a may have triangular-shaped micro patterns. For example, the plurality of micro patterns includes a first pattern 135a, a second pattern 135b, and a third pattern 135c, and a horizontal width W1 between the second pattern 135b and the third pattern 135c may be wider than a horizontal width W2 between the first pattern 135a and the second pattern 135b. The horizontal width W2 between an upper portion of the first pattern 135a and an upper portion of the second pattern 135b may be wider than the horizontal width W3 between a lower portion of the first pattern 135a and a lower portion of the second pattern 135b. A height H1 of the plurality of micro-patterns may be in the range of 50 to 300 µm.

Referring to FIGS. 9A and 9B, a high-voltage conductor 130b may have trapezoidal micro-patterns. For example, the plurality of micro patterns includes a first pattern 135a, a second pattern 135b, and a third pattern 135c, and a horizontal width W1 between the second pattern 135b and the third pattern 135c may be wider than a horizontal width W2 between the first pattern 135a and the second pattern 135b. A horizontal width W2 between an upper portion of the first pattern 135a and an upper portion of the second pattern 135b may be wider than a horizontal width W3 between a lower portion of the first pattern 135a and a lower portion of the second pattern 135b. A height H1 of the plurality of micro-patterns may be in the range of 50 to 300 µm.

Referring to FIGS. 10A and 10B, a high-voltage conductor 130c may have rectangular micro-patterns. For example, the plurality of micro patterns includes a first pattern 135a, a second pattern 135b, and a third pattern 135c, and a horizontal width W1 between the second pattern 135b and the third pattern 135c may be wider than a horizontal width W2 between the first pattern 135a and the second pattern 135b. A horizontal width W2 between a central portion of the first pattern 135a and a central portion of the second pattern 135b may be wider than a horizontal width W3 between a lateral side of the first pattern 135a and a lateral side of the second pattern 135b. A height H1 of the plurality of micro-patterns may be in the range of 50 to 300 µm.

Referring to FIGS. 11A and 11B, the high-voltage conductor 130b may have hemispherical micro-patterns. For example, the plurality of micro patterns includes a first pattern 135a, a second pattern 135b, and a third pattern 135c, and a horizontal width W1 between the second pattern 135b and the third pattern 135c may be wider than a horizontal width W2 between the first pattern 135a and the second pattern 135b. A horizontal width W2 between the upper center of the first pattern 135a and the upper center of the second pattern 135b may be wider than a horizontal width W3 between a bottom of a lateral side of the first pattern 135a and a bottom of a lateral side of the second pattern 135b. A height H1 of the plurality of micro-patterns may be in the range of 50 to 300 µm.

FIG. 12 is a diagram in which low temperature micro plasma generating devices are stacked according to an embodiment of the present disclosure.

Referring to FIGS. 12(a) and 12(b), in a low temperature micro plasma generating device 10, a diameter of a gas inlet of a first floating electrode and a diameter of a gas outlet of a second floating electrode are the same, so that a plurality of low temperature micro plasma generating devices can be stacked. That is, in a case where a plurality of low temperature micro plasma generating devices are stacked, the ozone generation amount and ozone generation efficiency may be increased once oxygen is introduced.

The foregoing is illustrative of embodiments and is not to be construed as limiting thereof, and the scope of the present disclosure may be indicated by the appended claims rather than by the foregoing detailed description. It is intended that all changes and modifications that are within the meaning and the range of the claims and also come from the equivalent concept of the claims should be interpreted within the scope of the present disclosure.

What is claimed is:

1. A low temperature micro plasma ozone generating device for generating ozone by sucking external air and causing the sucked air to react with plasma, the generating device comprising:
   a main body having an accommodating space therein;
   an ozone generating module installed in an internal accommodation space of the main body to generate ozone;
   an external air supply line installed to be connected to the ozone generating module from an outside of the main body and configured to supply external air of the main body to an inside of the ozone generating module;
   an ozone discharge line installed to extend from the inside of the ozone generating module to the outside of the main body to discharge the ozone generated by the ozone generating module to the outside of the main body; and
   a cooling fan installed on one side of the main body to supply the external air of the main body to an outer surface of the ozone generating module,
   wherein the ozone generating module comprises:
   a circular first floating electrode having an air inlet connected to the external air supply line;
   a second floating electrode coupled to the first floating electrode and having an ozone outlet installed to be connected to the ozone discharge line; and
   a high-voltage conductor disposed between the first floating electrode and the second floating electrode to generate plasma on a plurality of micro-patterns.

2. The low temperature micro plasma ozone generating device of claim 1, wherein the ozone generating module comprises:
   a first dielectric disposed between the first floating electrode and the high-voltage conductor; and
   a second dielectric disposed between the high-voltage conductor and the second floating electrode.

3. The low temperature micro plasma ozone generating device of claim 2, wherein:
   the ozone generating module is provided in plural and a plurality of ozone generating modules are installed in a stack,
   the ozone outlet of one ozone generating module is installed to be connected to the air inlet of another ozone generating module disposed thereunder,
   an air inlet of an uppermost ozone generating module is connected to the external air supply line, and
   an ozone outlet of a lowermost ozone generating module is connected to the ozone discharge line.

* * * * *